US008889877B2

(12) United States Patent
Goodman et al.

(10) Patent No.: US 8,889,877 B2
(45) Date of Patent: Nov. 18, 2014

(54) PROCESSES FOR PREPARING PYRIDINONE CARBOXYLIC ACID ALDEHYDES

(75) Inventors: Steven N. Goodman, King of Prussia, PA (US); Matthew David Kowalski, King of Prussia, PA (US); Douglas Matthew Mans, King of Prussia, PA (US); Huan Wang, King of Prussia, PA (US)

(73) Assignee: VIIV Healthcare Company, Research Triangle Park, NC (US)

( * ) Notice: Subject to any disclaimer, the term of this patent is extended or adjusted under 35 U.S.C. 154(b) by 0 days.

(21) Appl. No.: 13/636,237

(22) PCT Filed: Mar. 22, 2011

(86) PCT No.: PCT/US2011/029369
§ 371 (c)(1),
(2), (4) Date: Nov. 13, 2012

(87) PCT Pub. No.: WO2011/119566
PCT Pub. Date: Sep. 29, 2011

(65) Prior Publication Data
US 2013/0172551 A1    Jul. 4, 2013

Related U.S. Application Data

(60) Provisional application No. 61/316,421, filed on Mar. 23, 2010.

(51) Int. Cl.
C07D 213/803    (2006.01)
C07D 213/68     (2006.01)
C07D 498/14     (2006.01)
C07D 213/80     (2006.01)

(52) U.S. Cl.
CPC ............ *C07D 498/14* (2013.01); *C07D 213/68* (2013.01); *C07D 213/80* (2013.01)
USPC ........................................................ 546/327

(58) Field of Classification Search
CPC ......................... C07D 213/79; C07D 213/803
USPC ......................................................... 546/327
See application file for complete search history.

(56) References Cited

U.S. PATENT DOCUMENTS

| 4,524,149 A | 6/1985 | Lesher et al. |
| 4,603,144 A | 7/1986 | Campbell et al. |
| 4,735,964 A | 4/1988 | Campbell et al. |
| 4,769,380 A | 9/1988 | Jones, Jr. et al. |
| 4,812,474 A | 3/1989 | Campbell et al. |
| 5,688,815 A | 11/1997 | Zbinden |
| 6,426,418 B1 | 7/2002 | Tam et al. |
| 7,211,572 B2 | 5/2007 | Miyazaki et al. |
| 8,217,034 B2 | 7/2012 | Johns et al. |
| 8,552,187 B2 | 10/2013 | Johns et al. |
| 2001/0051732 A1 | 12/2001 | Muraoka et al. |
| 2004/0167124 A1 | 8/2004 | Chen et al. |
| 2005/0054645 A1 | 3/2005 | Miyazaki et al. |
| 2006/0019996 A1 | 1/2006 | Tucci et al. |
| 2006/0116356 A1 | 6/2006 | Cai et al. |
| 2006/0252944 A1 | 11/2006 | Lantzsch et al. |
| 2007/0072831 A1 | 3/2007 | Cai et al. |
| 2007/0249687 A1 | 10/2007 | Yoshida |
| 2007/0270485 A1 | 11/2007 | Wender et al. |
| 2008/0096886 A1 | 4/2008 | Tam et al. |
| 2008/0161271 A1 | 7/2008 | Yoshida et al. |
| 2008/0207562 A1 | 8/2008 | Zander et al. |
| 2009/0143356 A1 | 6/2009 | Yoshida et al. |
| 2009/0318421 A1 | 12/2009 | Johns et al. |
| 2011/0183940 A1 | 7/2011 | Johns et al. |
| 2011/0190236 A1 | 8/2011 | Johns et al. |
| 2011/0263855 A1 | 10/2011 | Johns et al. |
| 2011/0282055 A1 | 11/2011 | Yoshida et al. |
| 2012/0022251 A1 | 1/2012 | Sumino et al. |

FOREIGN PATENT DOCUMENTS

| CA | 2379370 | 9/2003 |
| EP | 0171814 | 8/1984 |
| EP | 0768302 B1 | 4/1997 |
| EP | 1544199 A1 | 6/2005 |
| EP | 2412709 A1 | 2/2012 |
| GB | 2280435 A | 2/1995 |
| JP | 2006342115 A | 12/2006 |
| JP | 2007509850 A | 4/2007 |
| JP | 2008540343 A | 11/2008 |
| WO | 98/54138 A1 | 12/1998 |
| WO | 2004024078 A2 | 3/2004 |
| WO | 2005/016927 A1 | 2/2005 |
| WO | 2005/087766 A1 | 9/2005 |
| WO | 2005/092099 A1 | 10/2005 |
| WO | 2006/030807 A1 | 3/2006 |
| WO | 2006/053429 A1 | 5/2006 |
| WO | 2006/066414 A1 | 6/2006 |
| WO | 2006/088173 A1 | 8/2006 |
| WO | 2006/116764 A1 | 11/2006 |
| WO | 2007/049675 A1 | 5/2007 |

(Continued)

OTHER PUBLICATIONS

Extended European Search Report issued Sep. 16, 2013 in corresponding EP application No. 11760040.3.
Sumino et al., Copending U.S. Appl. No. 13/814,333, filed Feb. 5, 2013 published as WO 2012/018065.
M. Ghandi et al., "A Novel Method for the Synthesis of Formyl and Hydroxymethyl Derivatives 4H-Pyran-4-One", Organic Preparations and Procedures International, vol. 34, No. 5; pp. 525-530; 2002.
S. Kukolja et al., "Studies on 4-Pyrones and 4-Pyridones. II. The Preparation and Rearrangement of 3-Allyloxy-4-Pyrone", Croatica Chemica Acta, vol. 33, pp. 229-233; 1961.
J.D. Thomas et al., "Overcoming Steric Effects in the Coupling Reaction of Alkyloxycarbonyloxymethyl (AOCOM) Halides with Phenols: An Efficient Synthesis of AOCOM Phenolic Prodrugs", Tetrahedron Letters, vol. 48, No. 1, pp. 109-112, Nov. 30, 2006.

(Continued)

Primary Examiner — Douglas M Willis
(74) Attorney, Agent, or Firm — Karen L. Prus

(57) ABSTRACT

The present invention relates to the preparation of pyridinone carboxylic acid aldehydes such as 5-methoxy-6-(methoxycarbonyl)-4-oxo-1-(2-oxoethyl)-1,4-dihydropyridine-3-carboxylic acid.

2 Claims, No Drawings

(56) References Cited

FOREIGN PATENT DOCUMENTS

| WO | 2008/103277 A2 | 8/2008 |
|---|---|---|
| WO | 2010/011812 A1 | 1/2010 |
| WO | 2010/011814 A1 | 1/2010 |
| WO | 2010/011819 A1 | 1/2010 |
| WO | 2010/068253 A1 | 6/2010 |
| WO | 2010/068262 A1 | 6/2010 |
| WO | 2010/110409 A1 | 9/2010 |
| WO | 2011/119566 A1 | 9/2011 |
| WO | 2012/018065 A1 | 2/2012 |

OTHER PUBLICATIONS

D. DeJohn et al., "Functionalization of Substituted 2(1H)- and 4(1H)-Pyridones. III. The Preparation of Substituted 6-Vinyl-1,2-Dihydro-2-Oxo- and 1,4-Dihydro-4-Oxo-3-Pyridinecarboxylic Acids Through the Chemistry of Pyridone Dianions", J. Heterocyclic Chem., vol. 20, pp. 1295-1302, Sep.-Oct. 1983.

J.C. Hastings et al., "Anti-Influenza Virus Activities of 4-Substituted 2,4-Dioxobutanoic Acid Inhibitors", Antimicrobial Agents and Chemotherapy, vol. 40, No. 5, pp. 1304-1307, May 1996.

O,D. Hensens et al., "Isolation and Structure of Flutimide, A Novel Endonuclease inhibitor of Influenza Virus", Tetrahedron Letters, vol. 36, No. 12, pp. 2005-2008, 1995.

J.D. Thomas, "Improving the Topical Delivery of Phenol-Containing Drugs: An Alkylcarbonyloxymethyl and Alkyloxycarbonyloxymethyl Prodrug Approach.". University of Florida, pp. 1-150, Dec. 31, 2006.

Y.K. Ko et al., "A New and Facile Synthesis of 2-Pyrdiones", Bull. Korean Chem. Soc., vol. 22, No. 2, pp. 234-236, 2001.

G. Chen et al., "Palladium-Catalyzed C-O Bond Formation: Direct Synthesis of Phenols and Aryl/Akyl Ethers from Activated Aryl Halides", Tetrahedron Letters, vol. 48, pp. 473-476, 2007.

B.W. McCleland et al., "Comparison N, N1-Diarysquaramides and N, N1-Diarylureas as Antagonists of the CXCR2 Chemokine Receptor", Bioorganic & Medicinal Chemistry Letters, vol. 17, pp. 1713-1717, 2007.

S.W. McCombie et al., "Generation and in Situ Acylation of Enaminone Anions: A Convenient Synthesis of 3-Carbethoxy-4(1H)-Pyridinones and 4-Pyrones and Related Compounds", J. Org. Chem., vol. 56, No, 16, pp. 4963-4967, 1991.

K.E.B. Parkes et al., "Use of a Pharmacophore Model to Discover a New Class of Influenza Endonuclease Inhibitors", J. Med. Chem., vol. 46, No. 7. pp. 1153-1164, 2003.

W.J. Ross et al., "The Synthesis and Rearrangement of Epoxypyrones", Tetrahedron Letters, vol. 22, No. 23, pp. 2207-2208, 1981.

S.B. Singh, "Total Synthesis of Flutimide, a Novel Endoculease Inhibitor of Influenza Virus," Tetrahedron Letters, vol. 36, No. 12, pp. 2009-2012, 1995.

J. Tomassini et al., "Inhibition of Cap (m7Gppp-Xm)-Dependent Endonuclease of Influenza Virus by 4-Substituted 2,4-Dioxobutanoic Acid Compounds", Antimicrobial Agents and Chemotherapy, vol. 38, No. 12, pp. 2827-2837, Dec. 1994.

J.S. Wai et al, Dihydroxypyridopyrazine-1,6-Dione HIV-1 Integrase Inhibitors, Bioorganic & Medicinal Chemistry Letters, vol. 17, pp. 5595-5599, 2007.

L.L. Woods et al., "reactions of Pyrones Catalyzed by Trifluoroacetic Acid", J. Org. Chem., pp. 1052-1053, Jun. 1960.

International Search Report issued May 17, 2011 in International (PCT) Application No. PCT/US11/29369.

Written Opinion mailed May 17, 2011 in International (PCT) Application No. PCT/US11/29369.

K.W. Anderson, et al., "The Selective Reaction of Aryl Halides with KOH: Synthesis of Phenols, Aromatic Ethers, and Benzofurans" J. Am. Chem. Soc., 128, pp. 10694-10695, Jun. 2006.

P.W. Groundwater, et al., "The cycloadditions of a series of 4H-pyran-4-ones 3c-3 with electron-rich dienes 11a, b to give reduced flavones 12 is described. The subsequent reactions of these reduced flavones with HCl, trifluoroacetic anhydride, ethyl anthranilate 19a and anthranilonitrile 19b is also described." J. Chem. Soc., Perkins Trans., vol. 1, pp. 163-169, 1997.

R. Kiyama et al., "Synthesis and Evaluation of Novel Nonpeptide Angiotensin II Receptor Antagonists: Imidazo [4: 5-c) pyridine Derivatives with an Aromatic Substituent" Chem. Pharm. Bull., vol. 43(3), pp. 450-460, 1995.

X. Rugang, Modern Organic Synthesis, pp. 72-74, East China University of Science and Technology Press, Jan. 31, 2007. (English Translation).

Ko, et al. ; "A New and Facile Synthesis of 2-Pyridones." Bull. Korean Chem. Soc., 2001, vol. 22 (2), p. 234.

Kocienski Protecting Groups, 3rd ed., Chapter 4, 2004, pp. 188, 230-237, 241.

Greene, Greene's Protective Groups in Organic Synthesis, 4th ed., 2007, pp. 24-28, 367-379, 992-993, 1005.

Third Party Observation for application No. EP20110760040, Mar. 31, 2014.

10756205.0 EP Search Report and Opinion, Nov. 11, 2013.

PCT/JP2010/055316 International Preliminary Report on Patentability and Written Opinion, Sep. 27, 2011.

Written Opinion Hungarian Patent Office Jun. 11, 2014.

PROCESSES FOR PREPARING PYRIDINONE CARBOXYLIC ACID ALDEHYDES

CROSS-REFERENCE TO RELATED APPLICATIONS

This application is filed pursuant to 35 U.S.C. §371 as a United States National Phase Application of International Application No. PCT/US2011/029369 filed Mar. 22, 2011, which claims priority from U.S. Provisional Application Ser. No. 61/316,421 filed Mar. 23, 2010.

FIELD OF THE INVENTION

The present invention relates to the preparation of carbamoylpyridone derivatives and intermediates which are useful as HIV integrase inhibitors.

BACKGROUND OF THE INVENTION

Compounds having HIV integrase inhibitory activity are described in WO 2006/116764 (corresponding to U.S. Ser. No. 11/919,386 assigned to Shionogi & Co. Ltd.). The compounds are disclosed as polycyclic carbamoylpyridone deriviatives. Processes for making them are also disclosed. Among the examples of these compounds, the following polycyclic carbamoylpyridone derivatives are included:

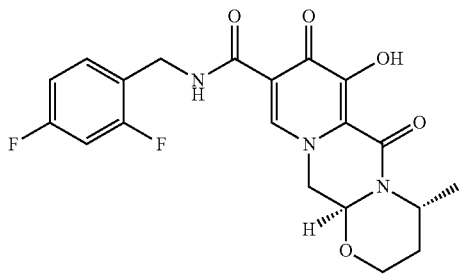

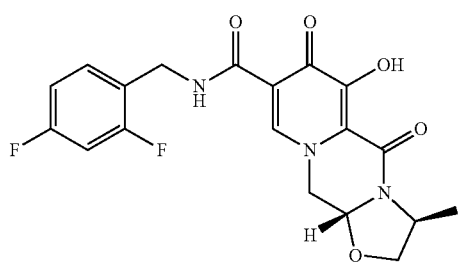

The processes disclosed for preparing these compounds are quite arduous, involving as many as 14 steps. It would therefore be an advance in the art to find ways of making these compounds with greater efficiency.

BRIEF SUMMARY OF THE INVENTION

The present invention provides an improved process for preparing the following compounds:

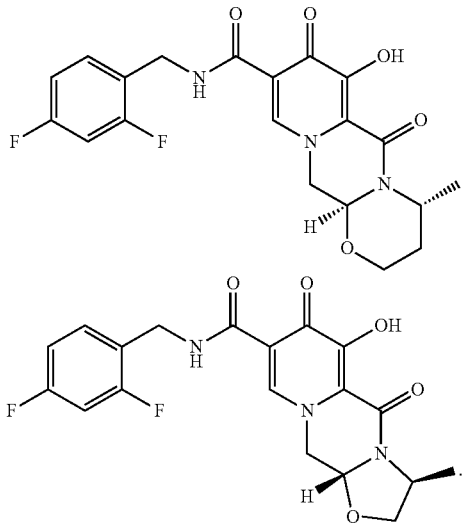

In one aspect, the present invention is a method comprising contacting methyl 3-{[2,2-bis(methyloxy)ethyl]amino}-2-[(methyloxy)acetyl]-2-propenoate (formula I):

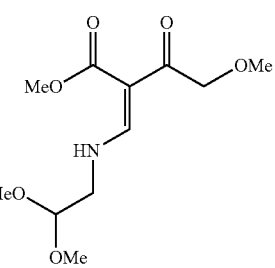

with an oxalate ester of formula II:

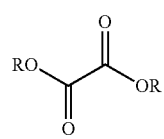

in the presence of $M^{+-}OR$, where R is alkyl, aryl, or benzyl; and $M^+$ is an alkali metal cation; to form a pyridinone of formula III:

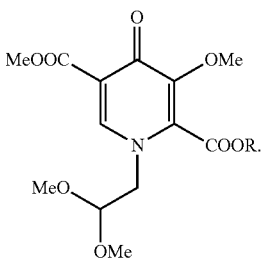

In a second aspect, the present invention method comprising selectively hydrolyzing a pyridinone of formula III:

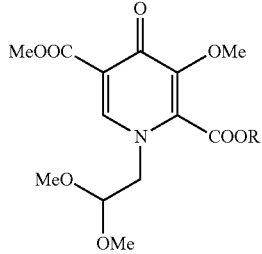

where R is alkyl, aryl, or benzyl
with a selective hydrolyzing reagent to form a pyridinone carboxylic acid of formula IV where R is alkyl, aryl, or benzyl:

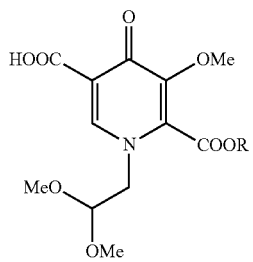

with greater than 90% selectivity.

In a third aspect, the present invention is a method comprising contacting a compound of formula VII:

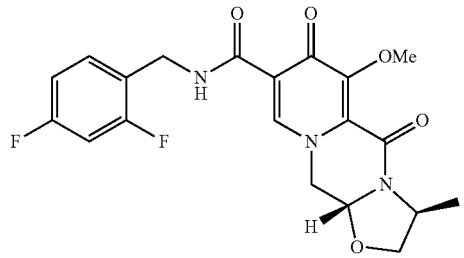

with a magnesium or lithium cation and a nucleophilic anion to form a compound of formula VIII:

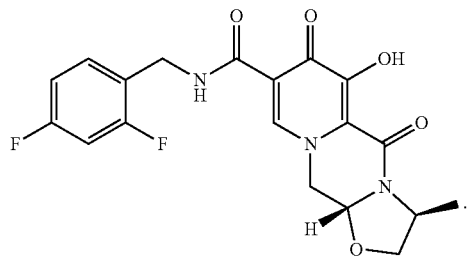

In a fourth aspect, the present invention is a compound selected from the group consisting of:

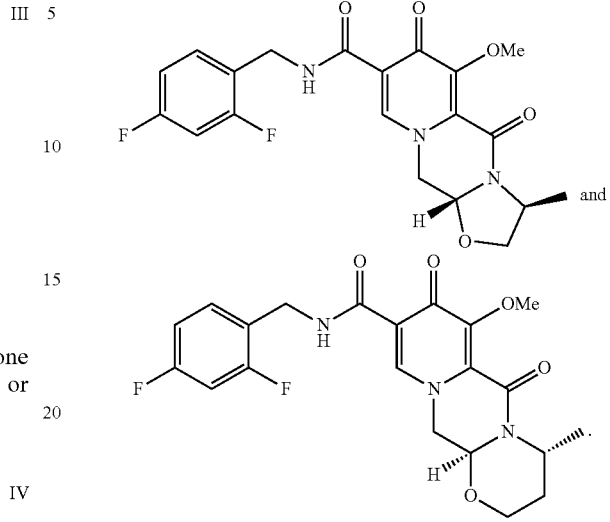

In a fifth aspect, the present invention is a process comprising contacting a compound of formula IV where R is alkyl, aryl, or benzyl:

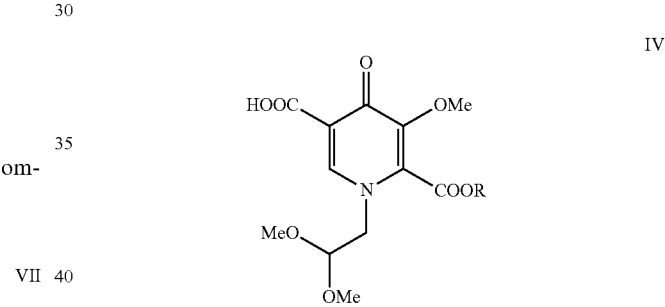

with acetic acid and a catalytic amount of a strong protic acid to form a pyridinone carboxylic acid aldehyde of formula V where R is alkyl, aryl, or benzyl:

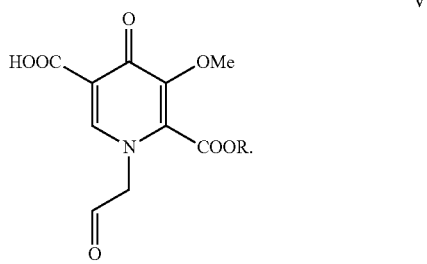

The process of the present invention is useful for the preparation of compounds with HIV integrase inhibitory activity.

DETAILED DESCRIPTION OF THE INVENTION

The following schematic illustrates a general process for the preparation of the compound of formula VIII, ((3S, 11aR)—N-[(2,4-difluorophenyl)methyl]-6-hydroxy-3-methyl-5,7-dioxo 2,3,5,7,11,11a-hexahydro[1,3]oxazolo[3,2-a]pyrido[1,2-d]pyrazine-8-carboxamide).

Scheme:

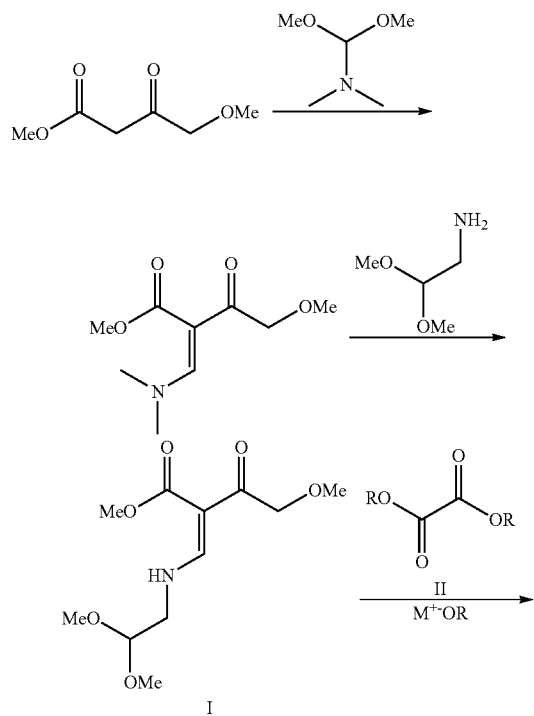

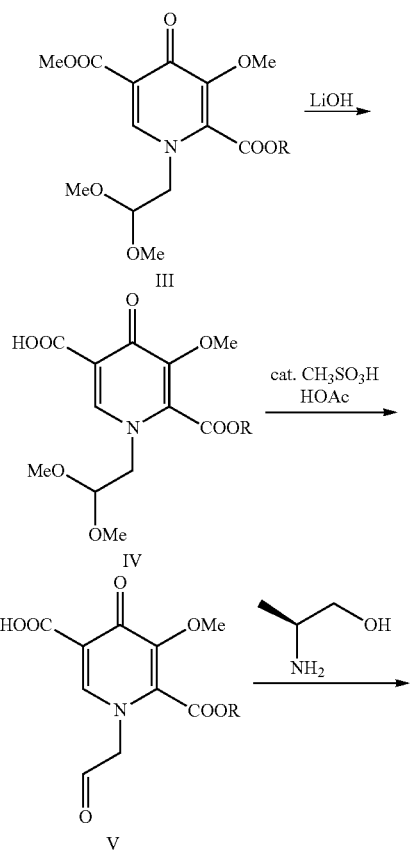

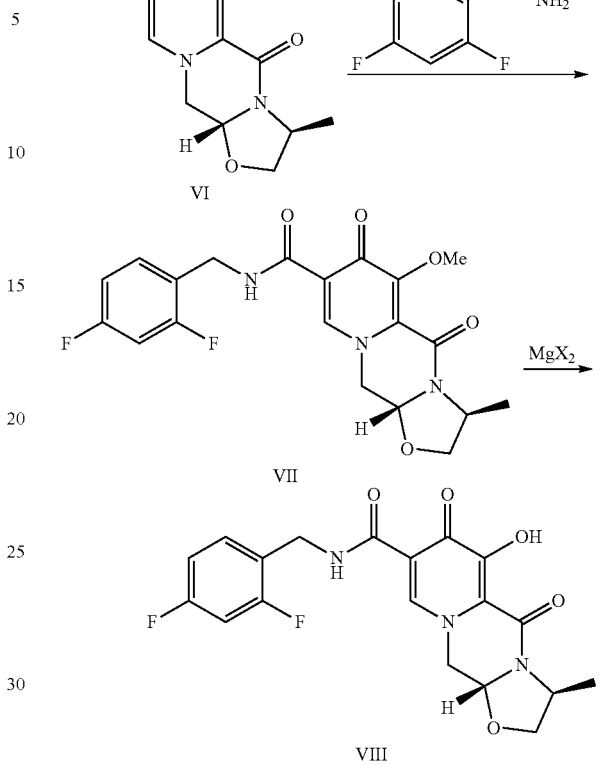

In the above schematic, 4-Methoxyacetoacetate is contacted with DMFDMA (N,N-dimethyl-1,1-bis(methyloxy)methanamine) under conditions sufficient to form methyl 3-(dimethylamino)-2-[(methyloxy)acetyl]-2-propenoate.

Reaction of this intermediate with aminoacetaldehyde dimethyl acetal results in the formation of methyl 3-{[2,2-bis(methyloxy)ethyl]amino}-2-[(methyloxy)acetyl]-2-propenoate (I).

Compound I is then contacted with oxalate ester (II) in the presence of $M^{+-}OR$ to form pyridinone (III). Each R is $C_1$-$C_5$-alkyl, aryl, or benzyl; $M^+$ is an alkali metal cation such as lithium, sodium, or potassium. Preferably, the alkali metal cation is lithium and the R group of the oxalate ester is the same as the R group from $M^{+-}OR$. Preferably R is a $C_1$-$C_5$-alkyl, especially a $C_1$-$C_2$-alkyl. Particularly preferred oxalate esters are dimethyl ethanedioate and diethyl ethanedioate. Particularly preferred alkali metal alkoxides are lithium methoxide and lithium ethoxide. Preferably, when the oxalate ester is dimethyl ethanedioate, the alkali metal alkoxide is lithium methoxide. Preferably, when the oxalate ester is diethyl ethanedioate, the alkali metal alkoxide is lithium ethoxide.

Pyridinone (III) is selectively hydrolyzed with LiOH to form pyridinone carboxylic acid (IV). Surprisingly, the methyl ester at the 5-position of pyridinone (III) is hydrolyzed with at least 90% selectivity over the ester at the 2-position.

Pyridinone carboxylic acid (IV) is contacted with acetic acid and a catalytic amount of a strong protic acid to form pyridinone carboxylic acid aldehyde (V). Examples of suitable strong protic acids include methanesulfonic acid, sulfuric acid, toluene sulfonic acid, and hydrochloric acid. Aldehyde (V) is then contacted with (2S)-2-amino-1-propanol to form ((3S,11aR)-3-methyl-6-(methyloxy)-5,7-dioxo-2,3,5,7,11,11a-hexahydro[1,3]oxazolo[3,2-a]pyrido[1,2-d]pyrazine-8-carboxylic acid) (VI).

Compound VI is contacted with 2.4-difluorobenzylamine under coupling conditions to form (3S,11aR)—N-[(2,4-difluorophenyl)methyl]-3-methyl-6-(methyloxy)-5,7-dioxo-2,3,5,7,11,11a-hexahydro[1,3]oxazolo[3,2-a]pyrido[1,2-d]pyrazine-8-carboxamide (VII).

Finally, compound VII is demethylated with a Lewis acid to form the product (3S,11aR)—N-[(2,4-difluorophenyl)methyl]-6-hydroxy-3-methyl-5,7-dioxo-2,3,5,7,11,11a-hexahydro[1,3]oxazolo[3,2-a]pyrido[1,2-d]pyrazine-8-carboxamide (VIII). Examples of suitable Lewis acids include magnesium, lithium, and calcium salts, as well as boron trihalides and trialkylsilyl halides. Preferred Lewis acids are magnesium and lithium salts. Magnesium salts include salts such as magnesium chloride, magnesium bromide, magnesium iodide, and magnesium sulfide. Lithium salts include salts such as lithium chloride, lithium bromide, lithium iodide, and lithium sulfide. Lithium bromide is preferred.

Alternatively, and in another aspect of the present invention, compound V can be contacted with (3R)-3-amino-1-butanol to form a compound of formula VIa:

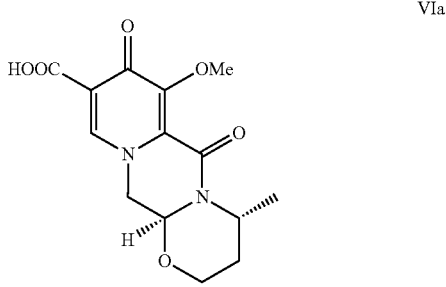 [SMILES: COc1c2n(cc(C(=O)O)c1=O)C[C@@H]1OCC[C@@H](C)N1C2=O]

VIa

Compound VIa can be reacted with 2,4-difluorobenzylamine under coupling conditions to form a compound of formula VIIa:

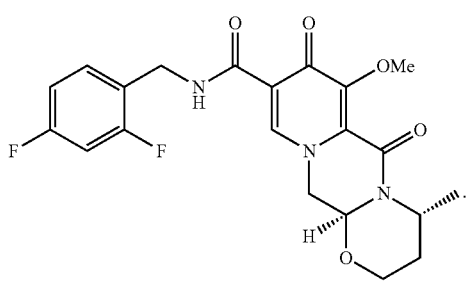

VIIa

Compound VIIa can be demethylated with $MgX_n$ or $LiX_n$ (wherein X is a halide, e.g., Br, Cl, F, or I) to form the compound of VIIIa:

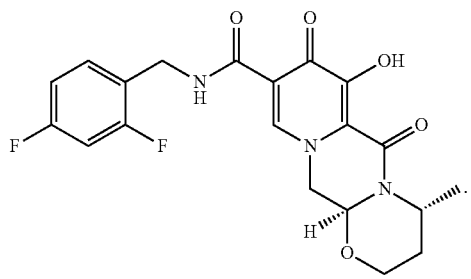

VIIIa

Examples

The following example illustrates the process of the present invention. Solvents and reaction conditions are not intended to limit the scope of the invention. Starting materials are known in the art and are readily prepared or commercially available. Preferably, chemicals employed in the examples were obtained commercially (from Aldrich®, for example).

A. 1-[2,2-Bis(methyloxy)ethyl]-5-(methyloxy)-6-[(methyloxy)carbonyl]-4-oxo-1,4-dihydro-3-pyridinecarboxylic acid A mixture of methyl 4-methoxyacetoacetate (20 mL) and DMFDMA (24 mL) was stirred at room temperature for 1.5 h. The reaction mixture was diluted with MeOH (50 mL) and aminoacetaldehyde dimethyl acetal (16.7 mL) was added. The mixture was stirred for 1 h at room temperature, concentrated, and then diluted with MeOH (113 mL). Dimethyl oxalate (45.66 g) was charged followed by portion-wise addition of LiH (2.15 g) while maintaining the reaction temperature below 25° C. The reaction content was heated to 40° C. for 14 h. The reaction mixture was cooled to −5° C. and LiOH (14.82 g) was added while maintaining the reaction temperature below 5° C. When addition was complete, the mixture was stirred for a further 2 h at 3-5° C. for 1 h. The reaction mixture was quenched with aqueous HCl (2 N, 367 mL), maintaining the reaction temperature below 5° C. When addition was complete, EtOAc (450 mL) was added and the mixture was warmed to 20° C. The reaction mixture was filtered and the aqueous layer discarded. Water (225 mL) was added and the organic layer was removed under reduced pressure. The product was collected by filtration and dried in a vacuum oven overnight at 50° C. The product was obtained as a solid.

B. (3S,11aR)-3-Methyl-6-(methyloxy)-5,7-dioxo-2,3,5,7,11,11a-hexahydro[1,3]oxazolo[3,2-a]pyrido[1,2-d]pyrazine-8-carboxylic acid 1-[2,2-bis(methyloxy)ethyl]-5-(methyloxy)-6-[(methyloxy)carbonyl]-4-oxo-1,4-dihydro-3-pyridinecarboxylic acid (22.54 g) was dissolved in 220 mL of $CH_3CN$. HOAc (20 mL) and $CH_3SO_3H$ (1.4 mL) were added at room temperature and the mixture was heated to 58-65° C. for 19.5 h. Alaninol (7.511 g) in $CH_3CN$ (15 mL) was added slowly and the resultant mixture was stirred at 64° C. for 18.5 h. The mixture was concentrated, and the residue was redissolved in $CH_2Cl_2$ (170 mL). HCl (1 N, 170 mL) was added and the layers were separated. The aqueous layer was extracted with $CH_2Cl_2$ (170 mL×2) and the organic layers were combined and concentrated. MeOH (50 mL) was added and the resultant mixture was again concentrated. MeOH (80 mL) was added and the resultant mixture was heated at reflux for 4 h, gradually cooled to 20° C. and held at 20° C. for 15 h. The product was collected by filtration and dried under vacuum.

C. (3S,11aR)—N-[(2,4-Difluorophenyl)methyl]-3-methyl-6-(methyloxy)-5,7-dioxo-2,3,5,7,11,11a-hexahydro[1,3]oxazolo[3,2-a]pyrido[1,2-d]pyrazine-8-carboxamide (3S,11aR)-3-Methyl-6-(methyloxy)-5,7-dioxo-2,3,5,7,11,11a-hexahydro[1,3]oxazolo[3,2-a]pyrido[1,2-d]pyrazine-8-carboxylic acid (3.00 g) and 1,1'-carbonyldiimidazole (CDI) (2.15 g) were slurried in 1,2-dimethoxyethane (DME) (30 mL). The mixture was heated to 80° C. for 1 h. The resulting solution was cooled to 20° C., then treated with 2,4-difluorobenzylamine (1.45 mL). After stirring for 1 h, the mixture was quenched with water (30 mL) and DME was removed under reduced pressure. The product was collected by filtration and dried in a vacuum oven overnight at 50° C. The product was obtained as a solid.

D. (3S,11aR)—N-[(2,4-Difluorophenyl)methyl]-6-hydroxy-3-methyl-5,7-dioxo-2,3,5,7,11,11a-hexahydro[1,3]oxazolo[33,2-a]pyrido[1,2-d]pyrazine-8-carboxamide (3S,11aR)—N-[(2,4-Difluorophenyl)methyl]-3-methyl-6-(methyloxy)-5,7-dioxo-2,3,5,7,11,11a-hexahydro[1,3]oxazolo[3,2-a]pyrido[1,2-d]pyrazine-8-carboxamide (193.1 mg) was dissolved in $CH_3CN$ (4 mL) and $MgBr_2$ (206.3 mg) was added. The mixture was heated to 50° C. for 2 h and quenched with HCl (0.2 N, 10 mL). The mixture was diluted with $CH_2Cl_2$ and pH further adjusted to ~1. The aqueous layer was extracted with $CH_2Cl_2$ (10 mL×2). The combined organic layers were dried and concentrated to afford the product.

Alternatively, the demethylation can be carried out with LiBr: (3S,11aR)—N-[(2,4-Difluorophenyl)methyl]-3-methyl-6-(methyloxy)-5,7-dioxo-2,3,5,7,11,11a-hexahydro[1,3]oxazolo[3,2-a]pyrido[1,2-d]pyrazine-8-carboxamide (8.609 g) was dissolved in THF (90 mL) and LiBr (3.942 g) was added. The mixture was heated to reflux for 12 h and quenched with $H_2SO_4$ (0.5 M, 94.467 g). The resultant suspension was stirred at 20° C. for 2 h and filtered. The solid product was re-slurried in water-THF (50 mL-50 mL) at 20° C. for 2 h. The product was collected by filtration, rinsed with water-THF (1-1, 30 mL), and dried under vacuum to afford the product.

What is claimed is:

1. A process for the preparation of a compound of formula (V)

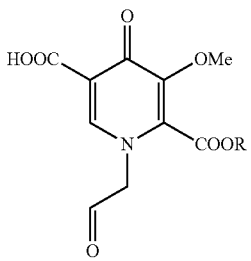

(V)

wherein R is alkyl, aryl, or benzyl,
comprising hydrolyzing a compound of formula (III)

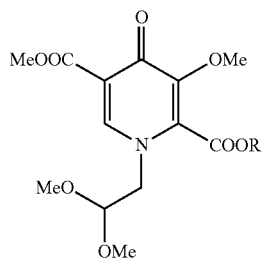

(III)

wherein R is alkyl, aryl, or benzyl,
in the presence of lithium hydroxide to form a compound of formula (IV)

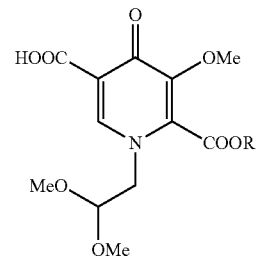

(IV)

wherein R is alkyl, aryl, or benzyl.

2. A process for the preparation of a compound of formula (V)

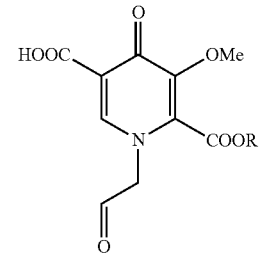

(V)

wherein R is alkyl, aryl or benzyl,
comprising contacting a compound of formula (IV)

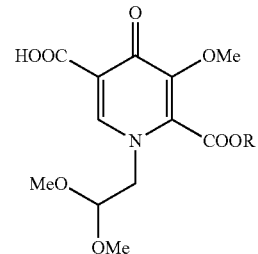

(IV)

wherein R is alkyl, aryl, or benzyl,
with acetic acid and a catalytic amount of a strong protic acid.

* * * * *